United States Patent [19]

Roszkowski

[11] Patent Number: 4,647,580

[45] Date of Patent: Mar. 3, 1987

[54] TREATMENT OF ALZHEIMER'S DISEASE

[75] Inventor: Adolph P. Roszkowski, Saratoga, Calif.

[73] Assignee: Syntex (U.S.A.) Inc., Palo Alto, Calif.

[21] Appl. No.: 756,872

[22] Filed: Jul. 18, 1985

[51] Int. Cl.$^4$ ............................................. A61K 31/36
[52] U.S. Cl. .................................................... 514/464
[58] Field of Search ....................................... 514/464

Primary Examiner—Stanley J. Friedman
Attorney, Agent, or Firm—Grant D. Green; Tom M. Moran; Alan M. Krubiner

[57] ABSTRACT

A treatment for senile dementia of the Alzheimer's type comprising administering to the patient a tertiary amine of the formula

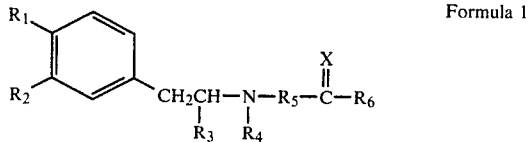

Formula 1 wherein $R^1$ is alkyl, alkoxy, alkylthio or dialkylamino hydroxyl, hydrogen, chlorine or fluorine;

$R^2$ is hydrogen, or when $R^1$ is hydrogen, alkyl, alkoxy, alkylthio, alkylthioamino, hydroxyl, chlorine or fluorine;

$R^3$ is 1 to 2 carbon alkyl;

$R^4$ is 1 to 3 carbon alkyl;

$R^5$ is an optionally branched 3 to 12 carbon alkylene; X is oxygen or ethylene dioxy; and $R^6$ is optionally branched or cyclic carbon group having less than eight carbons. The preferred compound is secoverine.

The administration of secoverine may be used in conjunction with the coadministration of a cholinergic enhancer, for example, in a combination with acetylcholinesterase inhibitors, muscarinic agonists or choline supplement therapy.

3 Claims, No Drawings

TREATMENT OF ALZHEIMER'S DISEASE

BACKGROUND OF THE INVENTION

This invention relates to treatments of senile dementia of the Alzheimer's type.

A new class of spasmolytics is disclosed in U.S. Pat. Nos. 3,996,245; 4,308,282; and 4,125,623. The tertiary amines disclosed in these three patents are all reported to have a strong and prolonged spasmolytic effect on the smooth musculature of the gastrointestinal tract, the urogenital tract and the bronchial system.

It has recently been reported in *Science* 228:115 (1985) that senile dementia of the Alzheimer's type is characterized by low levels of certain neuroreceptors in the brain. It has been found that the tertiary amines of the type reported useful for controlling spasmolytic activity in smooth musculature can be useful in relieving certain symptoms of senile dementia of the Alzheimer's type caused by the low levels of these neuroreceptors.

For a review of suggested treatments for Alzheimer's syndrome, see Crook T. and Gershon S. *Strategies for the Development of an Effective Treatment for Senile Dementia*, Mark Prowley Associates, New Canaan, Conn., 1981.

SUMMARY OF INVENTION

This invention provides a treatment of senile dementia of the Alzheimer's type. The affected patient is given an effective dose of a compound selected from the group

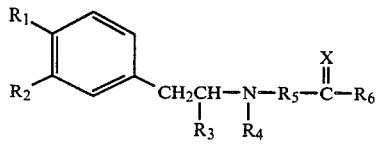

wherein
$R^1$ is alkyl, alkoxy, alkylthio or dialkylamino hydroxyl, hydrogen, chlorine or fluorine;
$R^2$ is hydrogen, or when $R^1$ is hydrogen, alkyl, alkoxy, alkylthio, alkylthioamino, hydroxyl, choline or fluorine;
$R^3$ is 1 to 2 carbon alkyl;
$R^4$ is 1 to 3 carbon alkyl;
$R^5$ is an optionally branched 3 to 12 carbon alkylene; X is oxygen or ethylene dioxy; and
$R^6$ is optionally branched or cyclic carbon group having less than eight carbons. The therapy can be in combination with acetylcholinesterase inhibitors, muscarinic agonists or choline supplemental therapy.

DETAILED DESCRIPTION OF THE INVENTION

Alkyl as used in this disclosure refers to carbon atoms having as specifically defined from 1 to 12 carbon atoms. The specific substituents may have less than 12 carbons. The alkyl groups may be branched or straight.

The alkoxy groups are alkyl groups, as defined above, connected through an oxygen to the remainder of the compound. Alkylthio groups are alkyl groups connected through a sulfur to the rest of the compound.

The tertiary nitrogen of the present compound may form salts. The pharmaceutically acceptable salts include those salts formed with the following acids: hydrochloric acid, hydrobromic acid, sulfuric acid, phosphoric acid, p-toluenesulfonic acid, benzoic acid, acetic acid, propionic acid, tartaric acid, succinic acid, citric acid, fumaric acid, maleic acid.

The compounds of this invention can be beneficially used in conjunction with several groups of compounds. Centrally acting mixed $M_1$ and $M_2$ agonists, for example, arecholine (see N. Stitaram, et al, *Science* 201:274-276 (1978), may be used. Another useful group of compounds are centrally acting acetylcholinesterase inhibitors, for example, physostigmine, for reversible inhibition, or nerve gases, for example sarin and soman, for irreversible inhibition. Another group of compounds is the precursor subtrates for the biosynthesis of acetylcholine, for example choline and lecithin.

The compounds can be brought into a form suitable for administration by methods known in the art. The compounds may be mixed with or dissolved in solid or liquid carrier materials. Resulting mixtures or solutions can be processed to pharmaceutical dosage forms, for example, tablets, capsules, coated tablets, pills and suppositories.

The preferred compound of this invention is secoverine, which is described in the USAN Directory of Adopted Names, (1985).

The dose of the active compound of this invention is the range of between 0.01 mg/kg and 10 mg/kg, preferably between 0.01 and 1.0 mg/kg. Suitable doses for humans that have been tried are 4 mg (Meshkinger and Hoehler, Drug Development Research, 5, 165-69, (1985)) and 30 mg (Elesameblah, et al., *Brit. J. Chem. Pharmacol*, 19:301-05 (1985).

Depending on the intended mode of administration, the compositions used may be in the form of solid, semi-solid or liquid dosage forms, such as, for example, tablets, suppositories, pills, capsules, powders, liquids, aerosols, suspensions or the like, preferably in unit dosage forms suitable for single administration of precise dosages. The compositions will include a conventional pharmaceutical carrier or excipient and an active compound of Formula I or the pharmaceutically acceptable acid addition salts and esters thereof and, in addition, may include other medicinal agents, pharmaceutical agents, carriers, adjuvants, etc.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

For the compounds of Formula I, either parenteral, oral or nasal (bronchial) administration is preferred, depending on the nature of the disorder being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium carbonate and the like. Such compositions take the form of solutions, suspensions, tablets, pills, capsules, powders, sustained release formulations and the like. Such compositions may contain 1%–95% active ingredient, preferably 25–70%.

Oral and nasal administration to the lungs can also be effected by aerosol delivery forms. For aerosol administration, the active ingredient is preferably supplied in finely divided form along with a surfactant and a propellant. Typical percentages of active ingredients are 0.01 to 20% by weight, preferably 0.04 to 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark Spans ®) and the polyoxyethylene and polyoxypropylene derivatives of these esters. Mixed esters, such as mixed or natural glycerides may be employed. The preferred surface-active agents are the oleates of sorbitan, e.g., those sold under the trademarks Arlacel C ® (Sorbitan sesquioleate), Span 80 ® (sorbitan monooleate) and Span 85 ® (sorbitan trioleate). The surfactant may constitute 0.1–20% by weight of the composition, preferably 0.25–5%.

EXAMPLES

The following examples show pharmaceutical preparations incorporating compounds of the present invention, for example, secoverine as the active ingredient.

EXAMPLE 1

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 2

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 3

| Ingredients | Quantity per tablet, mgs. |
|---|---|
| Active ingredient | 200 |
| cornstarch | 50 |
| lactose | 145 |
| magnesium stearate | 5 |

The above ingredients are mixed intimately and pressed into single scored tablets.

EXAMPLE 4

| Ingredients | Quantity per tablet, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE 5

| Ingredients | Quantity per tablet, mgs. |
|---|---|
| Active ingredient | 150 |
| lactose | 92 |

The above ingredients are mixed and introduced into a hard-shell gelatin capsule.

EXAMPLE 6

An injectable preparation buffered to a pH of 7 is prepared having the following composition:

| Ingredients | |
|---|---|
| Active ingredient | 0.2 g |
| $KH_2PO_4$ buffer (0.4 M solution) | 2 ml |
| KOH (1 N) | q.s. to pH 7 |

| Ingredients | |
|---|---|
| water (distilled, sterile) | q.s. to 20 ml |

A 1.0% solution may be raised to a pH of 5 to 6 without precipitation.

EXAMPLE 7

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

What is claimed is:

1. A method for treating a patient having Alzheimer's disease comprising administering to the patient a pharmaceutically effective amount of a compound of the formula:

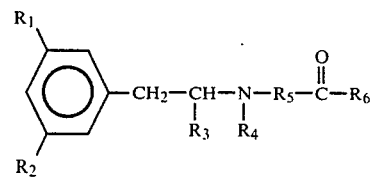

in which $R^1$ represents an alkyl group, an alkoxy group, an alkylthio group or dialkylamino group having up to 2 carbon atoms per substituent, a hydroxyl group, a hydrogen atom, a chlorine atom or a fluorine atom; and $R^2$ is a hydrogen atom; or $R^1$ represents a hydrogen atom in addition to one of the remaining meanings of $R^1$, while $R^1$ and $R^2$ may both represent alkoxy groups having up to 2 carbon atoms;

$R^3$ is an alkyl group having up to 2 carbon atoms;

$R^4$ is an alkyl group having up to 3 carbon atoms;

$R^5$ is a branched or nonbranched alkylene group having 3 to 12 carbon atoms;

$R^6$ is branched or nonbranched or cyclized alkyl group having up to 8 carbon atoms; and $R^5$ together with $R^6$ contains at least 6 carbon atoms; and salts formed with pharmaceutically acceptable acids; and a pharmaceutically acceptable carrier therefore.

2. The method of claim 1 wherein said compound is secoverine.

3. The method of claim 1 wherein the amount of said compound is between 0.01 mg/kg and 10.0 mg/kg.

* * * * *